United States Patent [19]

Servais et al.

[11] Patent Number: 4,783,560
[45] Date of Patent: Nov. 8, 1988

[54] STABILIZED COMPOSITIONS OF 1,1,1-TRICHLOROETHANE

[75] Inventors: Michel Servais, Kraainem; Jean Verbeyst, Zellik, both of Belgium

[73] Assignee: Solvay & Cie (Sociëtë Anonyme), Brussels, Belgium

[21] Appl. No.: 888,901

[22] Filed: Jul. 24, 1986

[30] Foreign Application Priority Data

Jul. 25, 1985 [FR] France ................................ 85 11531

[51] Int. Cl.$^4$ ........................ C07C 17/42; C07C 19/05
[52] U.S. Cl. .................................... 570/110; 570/111; 570/116; 570/118
[58] Field of Search ............... 570/104, 111, 116, 118, 570/110

[56] References Cited

U.S. PATENT DOCUMENTS

| 3,128,315 | 4/1964 | Hardies | 570/118 |
| 3,281,480 | 10/1966 | Hardies | 570/116 |
| 3,670,036 | 6/1972 | Vivion | 570/110 |

FOREIGN PATENT DOCUMENTS

| 35042 | 11/1975 | Japan | 570/111 |
| 6166127 | 12/1981 | Japan | 570/111 |

Primary Examiner—J. E. Evans
Attorney, Agent, or Firm—Spencer & Frank

[57] ABSTRACT

Stabilized compositions of 1,1,1-trichloroethane containing a mixture of two dialkoxyalkanes such as dimethoxymethane and 1,2-dimethoxyethane and at least one acid acceptor such as epoxybutane, and, if appropriate, a nitrated derivative such as nitromethane.

These compositions are well suited for degreasing metals and in the drycleaning of textiles.

9 Claims, No Drawings

STABILIZED COMPOSITIONS OF 1,1,1-TRICHLOROETHANE

The present invention relates to stabilized compositions of 1,1,1-trichloroethane, which can be used especially for degreasing metals and for drycleaning textiles.

It is known that 1,1,1-trichloroethane, which is used especially for degreasing metals, drycleaning textiles, and in aerosols, presents a particular problem of stability and of corrosion. The use of stabilizers which are commonly used for other chlorinated hydrocarbons to stabilize 1,1,1-trichloroethane generally does not give satisfactory results. This phenomenon has been attributed especially to the fact that there is a high reactivity between 1,1,1-trichloroethane and metals, such as aluminium, zinc and their alloys, and water. Consequently, many different stabilized compositions which are specific to 1,1,1-trichloroethane have been developed.

Thus, the stabilization of 1,1,1-trichloroethane by means of a mixture of stabilizers containing a dialkoxyalkane such as 1,2-dimethoxyethane, an aliphatic monohydric alcohol such as tert-butyl alcohol, a nitroalkane such as nitromethane and an epoxide such as epoxybutane, has been proposed in U.S. Pat. Nos. 3,281,480 and 3,128,315 of Pittsburgh Plate Glass.

Similarly, the stabilization of 1,1,1-trichloroethane by means of dimethoxymethane, alone or in combination with other costabilizers chosen especially from tertbutyl alcohol, epoxybutane and nitromethane, has been proposed in the French Patent Application 2,241,520 of La Société Chimique des Charbonnages.

Very large quantities of stabilizers are employed, in order to obtain a satisfactory stabilization.

Additionally, the alcohols present in the stabilized compositions lead to the formation of spots on evaporation.

None of the compositions proposed to date is really effective. Especially, no known composition of 1,1,1-trichloroethane has a satisfactory stability under extremely severe conditions such as those which exist during the simultaneous presence of light metals and water, and, more particularly, when water is present in large quantities, greater than the saturating value at the temperature and pressure under consideration.

The present invention aims at counteracting these drawbacks of known compositions by obtaining stabilized compositions of 1,1,1-trichloroethane of which the stability is satisfactory even under the most severe conditions of use.

To this end, the invention relates to stabilized compositions of 1,1,1-trichloroethane containing at least two dialkoxyalkanes of general formula $R_2-O-R_1-O-R_3$, in which $R_1$, $R_2$ and $R_3$ represent, independently from one another, saturated aliphatic radicals containing from 1 to 4 carbon atoms.

Usually, $R_1$ represents a saturated aliphatic radical of formula $-(CH_2)_n-$ in which n is an integer of 1 to 4; preferably, n is equal to 1 or 2.

Usually, $R_2$ and $R_3$ represent saturated aliphatic radicals, of formula $-(CH_2)_r-CH_3$ in which R is an integer of 0 to 3; preferably R is equal to 0.

Good results were obtained when the compositions contain dimethoxymethane and 1,2-dimethoxyethane simultaneously.

The quantity of each dialkoxyalkane present in the compositions according to the invention usually varies between 0.1 and 100 grams per liter of 1,1,1-trichloroethane. Preferably, this quantity is of between 1 and 75 grams per liter. Quantities of between 5 and 50 grams per liter are most particularly preferred.

The quantities of the different dialkoxyalkanes present in the mixture may be identical or different. Good results were obtained when dimethoxymethane and 1,2-dimethoxyethane are employed in molar ratios of between 0.1 and 10, and preferably of between 0.2 and 5.

Furthermore, the compositions of the invention advantageously contain at least one acid acceptor such as epoxidated compounds.

The term "epoxidated compound" refers to saturated or unsaturated aliphatic compounds containing at least one epoxide group in their molecule. Preferably, the compositions according to the invention contain saturated aliphatic epoxides containing from 3 to 6 carbon atoms in their molecule such as epoxypropane, epoxybutane, 2-methylepoxypropanes, 2-methylepoxybutanes, glycidol and epichlorohydrin. Good results were obtained with 2-methyl-2,3-epoxybutane and epoxybutane which is most particularly preferred.

The total quantity of epoxidated compound present in the compositions according to the invention usally varies between 0.01 and 50 grams per liter. Preferably, this quantity is of between 0.1 and 20 grams per liter. Quantities of between 1 and 10 grams per liter are most particularly preferred.

In addition to the abovementioned compounds, the compositions according to the invention may contain nitrated derivatives such as nitroalkanes containing from 1 to 4 carbon atoms in their molecule. Good results were obtained with nitromethane, nitroethane and nitropropanes 1 or 2. Nitroethane and especially nitromethane, and the mixtures of these two compounds are most particularly preferred.

The quantities of nitrated derivatives are the same as those stated for the epoxidated compounds.

Other compounds, and especially nitrates such as alkyl nitrates containing from 1 to 5 carbon atoms, amines such as aliphatic amines containing from 2 to 6 carbon atoms, pyrroles, quinones and other aromatic compounds such as phenol and its derivatives and toluene, or aliphatics such as diisobutylene may also be incorporated as costabilizers in the formula which is finally employed for stabilizing 1,1,1-trichloroethane.

These different stabilizers used are generally present in highly variable quantities of between 0.001 and 50 g/l of 1,1,1-trichloroethane, and preferably in quantities of between 0.1 and 30 g/l.

The stabilized compositions of 1,1,1-trichloroethane according to the invention are particularly well suited for applications which require a good stabilization of the 1,1,1-trichloroethane under consideration and the presence of the lowest possible total quantity of stabilizers simultaneously. They are advantageously used for hot, cold or vapour phase degreasing of metals and most particularly for the cold degreasing of metals, given that the stabilized compositions of 1,1,1-trichloroethane according to the invention have the characteristic of wetting metallic objects very effectively. Additionally, as these compositions do not contain alcohol, they do not leave any marks on evaporation.

The compositions according to the invention are also highly suitable for recycling.

The examples which follow are in no way of a limiting nature.

EXAMPLE 1

This example is carried out in order to demonstrate the improved stability observed with the compositions according to the invention (Test 1) in comparison with other compositions of the same type which contain a single dialkoxyalkane (Tests 2 and 3) under severe operating conditions, that is to say, in the presence of light metals and water. The quantities of products employed and the results obtained in the different tests are collectively presented in Table I below.

Test 1: Composition according to the invention 200 cm$^3$ of 1,1,1-trichloroethane, stabilized by means of 5 g/l of nitromethane, 5.7 g/l of 1,2-epoxybutane, 20 g/l of dimethoxymethane and 25 g/l of 1,2-dimethoxyethane are introduced into a Soxhlet apparatus consisting of a 500 cm$^3$ round-bottomed flask and a 100 cm$^3$ reservoir without the filter cartidge, which is equipped for heating with a heating mantle.

2 cm$^3$ of demineralized water are then introduced.

Testpieces, 40×8×3 mm in size, made of an aluminium alloy containing 4.5% copper, 0.6% magnesium and 0.6% manganese (alloy AU 4 G-T4) are then introduced, while maintaining the mixture at ambient temperature; one testpiece is immersed in the Soxhlet reservoir and a second in the condenser.

The flask is then heated so as to obtain an emptying of the reservoir every thirty minutes ($\simeq$2 minutes).

After 72 h of boiling, the flask is cooled to a temperature of 20° C., and the flask and the reservoir are emptied.

The flask, the reservoir, the condenser and the testpieces are carefully rinsed with demineralized water and the rinsing liquid is used for the extraction of the 1,1,1-trichloroethane recovered.

The acid uptake is determined using the organic phase.

The aqueous extract is made up to 250 cm$^3$ in a volumetric flask and the Cl$^-$ ions formed are determined by mercurimetry.

The testpieces are brushed under water using a non-metallic hard brush; after rinsing with demineralized water, they are then dried with acetone, and then weighed to the nearest 0.1 mg. The results observed are presented in Table I below. Each test was replicated twice.

Furthermore, no trace is observed on these testpieces on evaporating the stabilized 1,1,1-trichloroethane.

Tests 2 and 3: Compositions for comparison

Tests 2 and 3 are identical to Test 1 as regards the conditions of operation.

In Test 2, the 1,1,1-trichloroethane is stabilized by means of 5 g/l of nitromethane, 5.7 g/l of 1,2-epoxybutane and 45 g/l of dimethoxymethane.

Test 3 is carried out by means of 5 g/l of nitromethane, 5.7 g/l of 1,2-epoxybutane and 45 g/l of 1,2-dimethoxyethane.

TABLE 1

| | TEST 1 | | TEST 2 | | TEST 3 | |
|---|---|---|---|---|---|---|
| | 1 | 2 | 1 | 2 | 1 | 2 |
| Stabilizers g/l | | | | | | |
| Dimethoxymethane | 20 | 20 | 45 | 45 | 0 | 0 |
| 1,2-Dimethoxyethane | 25 | 25 | 0 | 0 | 45 | 45 |
| Nitromethane | 5 | 5 | 5 | 5 | 5 | 5 |
| 1,2-Epoxybutane | 5.7 | 5.7 | 5.7 | 5.7 | 5.7 | 5.7 |
| Results after test | | | | | | |
| Loss in acid uptake % | 9 | 13 | 59 | 77 | 77 | 81 |
| Cl$^-$ formed meq/l | 2.3 | 1 | 63 | 52 | 74 | 56 |
| Loss in weight of the testpieces g/m$^2$/day | | | | | | |
| Soxhlet | 17 | 0 | 122 | 129 | 167 | 132 |
| Condenser | 1.4 | 0.1 | 160 | 154 | 220 | 185 |

Therefore, from an examination of the results in Table 1, it may be concluded that in the presence of water and aluminium, the composition according to the invention (Test 1), compared to the other compositions. (Tests 2 and 3) which contain a single dialkoxyalkane, is 6 to 8 times more efficient from the point of view of acid uptake, forms 25 to 75 times less Cl$^-$ ions and corrodes 10 to 200 times less the testpieces made of aluminium alloy in contact with water and with 1,1,1-trichloroethane at the same time.

EXAMPLE 2

This example is carried out in order to demonstrate the improved stability observed with compositions according to the invention (Test 1) containing a mixture of dimethoxymethane, 1,2-dimethoxyethane and epoxybutane in comparison with other compositions which contain a single dialkoxyalkane (dimethoxymethane), an alcohol and epoxybutane (Test 2).

Test 1: Composition according to the invention

In this test, the 1,1,1-trichloroethane is stabilized by means of:

30 g/l of dimethoxymethane,
20 g/l of 1,2-dimethoxyethane and
5.7 g/l of 1,2-epoxybutane.

The test is carried out under the same operating conditions as described in Example 1, Test 1.

The results obtained are as follows:
loss in acid uptake: 78%
Cl$^-$ ions formed: 66 meq/l
loss in weight of testpieces in g/m$^2$/day:
* Soxhlet: 129
* cool: 143

Test 2: Compositions for comparisons

In these tests, the 1,1,1-trichloroethane is stabilized by means of:
(a)
30 g/l of dimethoxymethane,
20 g/l of tert-butyl alcohol and
5.7 g/l of 1,2-epoxybutane.
(b)
30 g/l of 1,2-dimethoxyethane,
20 g/l of tert-butyl alcohol and
5.7 g/l of 1,2-epoxybutane.

The test is again carried out under the same operating conditions as described in Example 1, Test 1.

In both cases, a violent decomposition is observed.

Therefore, from the comparison of the results obtained in Test 1 and Test 2, it may be concluded that the compositions of the invention give acceptable results in the absence of nitromethane in the test used, whereas a composition which contains only a single dialkoxyalkane confers no stability on the 1,1,1-trichloroethane in the absence of nitromethane.

EXAMPLE 3

This example is carried out in order to demonstrate that, even in the absence of nitroalkane, the compositions according to the invention meet the requirements of official tests for the approval of halogenated solvents for degreasing light metals in Germany.

Test 1: Composition according to the invention

In this test, the 1,1,1-trichloroethane is stabilized by means of:
10 g/l of dimethoxymethane,
31 g/l of 1,2-dimethoxyethane,
5.2 g/l of epoxybutane.

With this composition the following test is carried out, known in Germany as the BAM I (Bundesanstalt für Materialprüfung) test.

100 cm$^3$ of stabilized 1,1,1-trichloroethane are introduced into a 500 cm$^3$ round-bottomed flask fitted with a side-tube which enables the temperature of the liquid to be measured by means of a thermocouple.

100 cm$^3$ of toluene are then introduced into the flask and the contents are mixed.

18 g of aluminium tinsels (tinsels from 0.1 to 1 mm in diameter) and 0.7 g of non-agglomerated, sublimated, anhydrous AlCl$_3$ are added to this mixture.

This mixture is subjected to boiling at the reflux temperature for 9 h in a 500 cm$^3$ flask, heated in an oil bath, which is thermostatically maintained at 40° C. above the boiling temperature of the 1,1,1-trichloroethane.

The boiling is stopped for 15 h.

The mixture is then once again subjected to boiling at the reflux temperature for 21 h.

The 1,1,1-trichloroethane does not meet the requirements of the test BAM I when it undergoes an exothermic decomposition or when it continues to decompose after the removal of the heat source.

The stabilized composition according to the invention does not undergo an exothermic decomposition during the 9 h of boiling, the 15 h of rest followed by the 21 h of boiling.

Test 2: Composition for comparison

In this test, the 1,1,1-trichloroethane is stabilized by means of:
31 g/l of 1,2-dimethoxyethane,
21 g/l of tert-butyl alcohol and
5.2 g/l of 1,2-epoxybutane.

This composition is subjected to the same stability test as the composition of Example 3, Test 1.

This composition does not undergo exothermic decomposition during the 9 hours of boiling and the 15 hours of rest, but decomposes after 10 hours of the second boiling.

Test 3: Composition for comparison

In this test, the 1,1,1-trichloroethane is stabilized by means of:
31 g/l of 1,2-dimethoxyethane,
21 g/l of 2-methyl-3-buten-2-ol,
5.2 g/l of 1,2-epoxybutane.

This composition is also subjected to the same test as those of Tests 1 and 2 above.

This composition decomposes after only 5.5 hours of boiling.

From the comparison of the results obtained in the Tests 1, 2 and 3 above, it may be concluded that the only composition not containing nitromethane which meets the requirements of the official test BAM I is the composition according to the invention (Test 1), despite the fact that the total quantity of stabilizers is less than those in Tests 2 and 3.

EXAMPLE 4

This example is carried out to demonstrate that, even in the absence of nitromethane, the compositions according to the invention also meet the requirements of the strict official test BAM IV, used in Germany for the approval of halogenated solvents for degreasing light metals.

The composition of 1,1,1-trichloroethane contains:
20 g/l of dimethoxymethane,
50 g/l of 1,2-dimethoxyethane and
5.7 g/l of 1,2-epoxybutane.

500 cm$^3$ of stabilized 1,1,1-trichloroethane is divided into three equal fractions by simple distillation. The final fraction is not distilled and the rate of distillation is of the order of 20 cm$^3$ per minute.

The test described in Example 3 Test 1 is now carried out on each fraction.

The three fractions of the composition do not undergo decomposition during the 9 hours of boiling, the 15 hours of rest and the 21 hours of final boiling. Therefore, the composition according to the invention meets the requirements of the test BAM IV perfectly, in spite of the absence of nitroalkane.

We claim:

1. Stabilized compositions of 1,1,1,-trichloroethane characterized in that they contain at least two dialkoxyalkanes and at least one epoxidated compound, wherein each dialkoxyalkanes is present in quantities of between 0.1 and 100 g per liter of 1,1,1-trichloroethane and the at least one epoxidated compound is present in quantities of between 0.01 and 50 g per liter of 1,1,1-trichloroethane, wherein the at least two dialkoxyalkanes have the general formula R$_2$—O—R$_1$—O—R$_3$ in which R$_1$, R$_2$ and R$_3$ represent, independently from one another, saturated aliphatic radicals containing from 1 to 4 carbon atoms, wherein R$_1$ represents a saturated aliphatic radical of formula —(CH$_2$)$_n$ in which n is an integer of 1 to 4 and R$_2$ and R$_3$ represent saturated aliphatic radicals of formula —(CH$_2$)$_r$CH$_3$ in which r is an interger of 0 to 3, and wherein the at least one epoxidated compound is a saturated aliphatic epoxide containing from 3 to 6 carbon atoms.

2. Compositions according to claim 1, characterized in that one of the at least two dialkoxyalkanes is dimethoxymethane.

3. Compositions according to claim 1, characterized in that one of the at least two dialkoxyalkanes is 1,2-dimethoxyethane.

4. Compositions according to claim 1, characterized in that they contain dimethoxymethane and 1,2-dimethoxyethane at the same time.

5. Compositions according to claim 4, characterized in that the dimethoxymethane and the 1,2-dimethoxyethane are employed in molar ratios of between 0.1 and 10.

6. Compositions according to claim 1, characterized in that they additionally contain at least one nitrated derivative.

7. Compositions according to claim 6, characterized in that the at least one epoxidated compound is selected from 2-methyl-2,3-epoxybutane and 1,2-epoxybutane and that the at least one nitrated derivative is selected from nitromethane and nitroethane.

8. Compositions according to claim 6, characterized in that the at least one nitrated derivative is present in quantities of between 0.01 and 50 g per liter of 1,1,1-trichloroethane.

9. Compositions according to claim 1, characterized in that the at least one epoxidated compound is selected from 2-methyl-2,3-epoxybutane and 1,2-epoxybutane.

* * * * *